US011918289B2

(12) United States Patent
Azar et al.

(10) Patent No.: US 11,918,289 B2
(45) Date of Patent: Mar. 5, 2024

(54) PERIOCULAR ENVIRONMENT MONITORING IN A HEADSET

(71) Applicant: Twenty Twenty Therapeutics LLC, South San Francisco, CA (US)

(72) Inventors: Dimitri Azar, San Francisco, CA (US); Kirk Gossage, Pacifica, CA (US); Sam Kavusi, Menlo Park, CA (US); Prachi Shah, South San Francisco, CA (US)

(73) Assignee: Twenty Twenty Therapeutics LLC, South San Francisco, CA (US)

( * ) Notice: Subject to any disclaimer, the term of this patent is extended or adjusted under 35 U.S.C. 154(b) by 556 days.

(21) Appl. No.: 16/872,649

(22) Filed: May 12, 2020

(65) Prior Publication Data

US 2020/0359886 A1 Nov. 19, 2020

Related U.S. Application Data

(60) Provisional application No. 62/847,715, filed on May 14, 2019.

(51) Int. Cl.
*A61B 3/10* (2006.01)
*A61B 3/00* (2006.01)
(Continued)

(52) U.S. Cl.
CPC ............ *A61B 3/101* (2013.01); *A61B 3/0008* (2013.01); *A61B 5/6803* (2013.01); *A61B 2562/0271* (2013.01); *A61B 2562/029* (2013.01)

(58) Field of Classification Search
CPC ......... A61B 3/02; A61B 3/1025; A61B 3/102; A61B 3/113; A61B 3/1015; A61B 3/1225; A61B 3/024; A61B 5/0022; A61B 5/1455
(Continued)

(56) References Cited

U.S. PATENT DOCUMENTS 8,909,327 B1 12/2014 Bosworth
10,198,068 B2 2/2019 Holz et al.
(Continued)

FOREIGN PATENT DOCUMENTS

CN 104024984 A 9/2014
CN 108445634 A 8/2018
(Continued)

OTHER PUBLICATIONS

International Search Report and Written Opinion received in corresponding Patent Cooperation Treaty Application No. PCT/US2020/032704, dated Aug. 19, 2020, 14 pages.

*Primary Examiner* — Dawayne Pinkney
(74) *Attorney, Agent, or Firm* — Aikin & Gallant, LLP

(57) ABSTRACT

Disclosed is a headset for monitoring periocular humidity, the headset including a housing configured to be positioned on a user's face and defining a periocular air space. The headset includes a humidity sensor configured to measure a humidity of air within the periocular air space, and an ophthalmic testing unit configured to measure a physiological parameter of an eye of the user. The headset further includes a processor coupled to the humidity sensor and the ophthalmic testing unit. The processor is configured to receive the measured humidity and the measured physiological parameter, and determine an ophthalmic condition based on the measured humidity and the measured physiological parameter.

23 Claims, 14 Drawing Sheets

(51) Int. Cl.
  *A61B 3/02* (2006.01)
  *A61B 3/12* (2006.01)
  *A61B 5/00* (2006.01)

(58) Field of Classification Search
  USPC ....... 351/206, 200, 205, 209, 210, 221–223, 351/246
  See application file for complete search history.

(56) References Cited

U.S. PATENT DOCUMENTS

| | | | |
|---|---|---|---|
| 2004/0225204 A1* | 11/2004 | Endo | A61B 3/101 600/307 |
| 2015/0356781 A1 | 12/2015 | Miller | |
| 2017/0000329 A1 | 1/2017 | Samec et al. | |
| 2017/0007182 A1 | 1/2017 | Samer | |
| 2019/0374100 A1* | 12/2019 | Okazaki | A61B 3/14 |
| 2020/0138669 A1* | 5/2020 | Berdahl | A61F 9/029 |

FOREIGN PATENT DOCUMENTS

| | | | | |
|---|---|---|---|---|
| CN | 110709123 A | * | 1/2020 | ........... A61F 9/0026 |
| CN | 113749610 A | * | 12/2021 | ........... A61B 3/0025 |
| GB | 2474265 | | 4/2011 | |
| WO | WO 2017/156050 | | 9/2017 | |

* cited by examiner

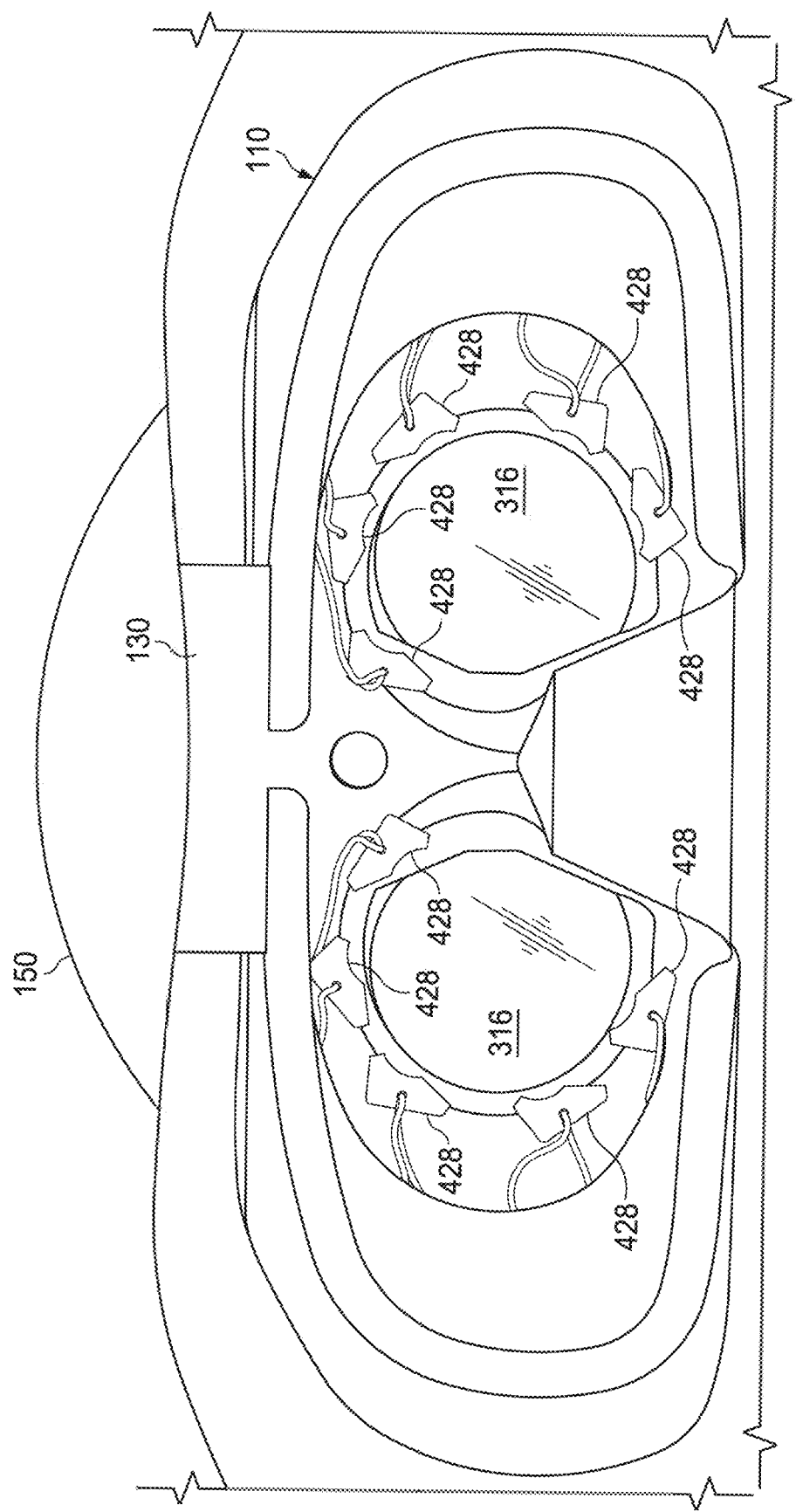

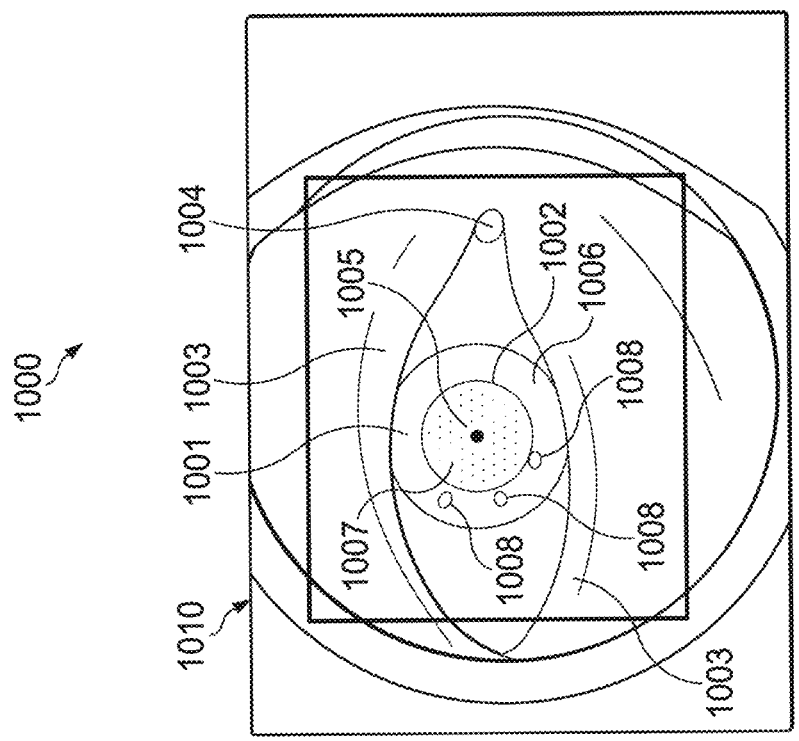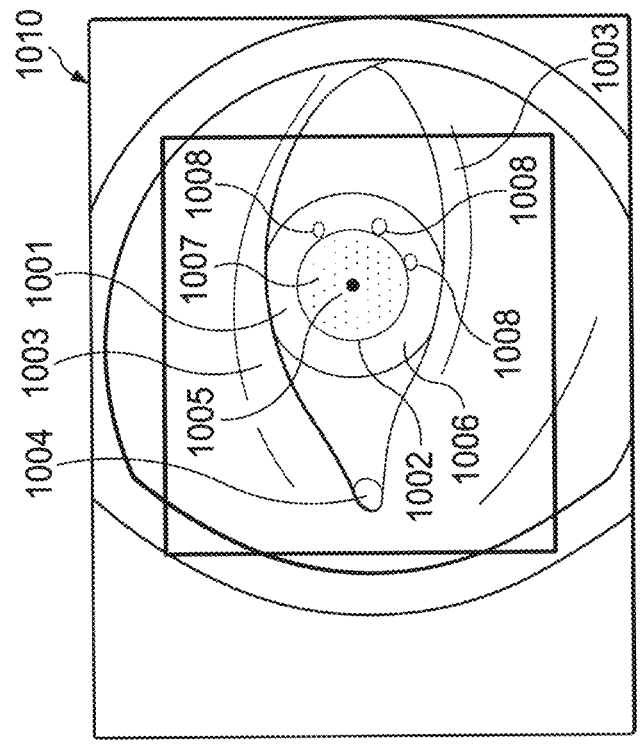
Fig. 8

PERIOCULAR ENVIRONMENT MONITORING IN A HEADSET

CROSS-REFERENCE TO RELATED APPLICATIONS

The present application claims the benefit of and priority to U.S. Provisional Patent Application No. 62/847,715, filed May 14, 2019, the entirety of which is hereby incorporated by reference.

TECHNICAL FIELD

The subject matter described herein relates to devices and methods for monitoring and control of periocular air temperature and/or humidity in a headset. In particular, the headset for controlling periocular humidity can be adapted for testing of dry eye and other ophthalmic conditions, but is not limited to such applications.

BACKGROUND

Dry eye is a medical condition that may be caused by blockage or reduced output of the tear ducts or Meibomian glands, reduced production of ocular mucus, or other causes. The condition may be triggered, for example, by aging, menopause, rheumatoid arthritis, neurological conditions, immunological conditions, or the use of certain drugs. The condition may be treated through the use of hormones, steroids, antibiotics, lubricating drops or ointments, wearing airtight goggles, temporary medical occlusion of ducts, or the unclogging of glands.

Dry eye may be diagnosed by primary care physicians through an interview process, but determining the severity, cause, and proper treatment of dry eye typically requires an ophthalmologist visit that may last several hours, with attendant costs and inconvenience. The symptoms, severity, and treatments of dry eye may depend on the temperature and humidity of the environment in which the diagnosis is being performed, which are highly variable. Accordingly, testing results may vary significantly, leading to different possible diagnostic outcomes. Accordingly, there is a need for devices capable of testing or grading dry eye or other ophthalmic conditions in environments with varying humidity and/or temperature. There is also a need for such devices and associated methods that are more convenient and/or less costly than current technologies for testing or grading dry eye or other ophthalmic conditions.

The information included in this Background section of the specification, including any references cited herein and any description or discussion thereof, is included for technical reference purposes only and is not to be regarded as subject matter by which the scope of the disclosure is to be bound.

SUMMARY

Disclosed herein are devices and methods for monitoring and/or control of periocular air temperature and/or humidity in a headset, i.e., in the periocular air space. One general aspect includes a headset for monitoring periocular humidity, including a housing configured to be positioned on a user's face, the housing defining a periocular air space. In some aspects, the headset may be configured to regulate air conditions within the periocular air space. The headset includes further components for monitoring the environment in the air space between the headset and the user's eye. A processor of the headset is configured to: receive data or measurements of the environment within and/or around the headset, and determine an ophthalmic condition based on the measured data or measurements.

According to one embodiment of the present disclosure, a headset for monitoring periocular humidity, comprises: a housing configured to be positioned on a user's face, the housing defining a periocular air space; a humidity sensor configured to measure a humidity of air within the periocular air space; an ophthalmic testing unit configured to measure a physiological parameter of an eye of the user; and a processor coupled to the humidity sensor and the ophthalmic testing unit, the processor configured to: receive the measured humidity and the measured physiological parameter; and determine an ophthalmic condition based on the measured humidity and the measured physiological parameter.

In some embodiments, the headset further includes a humidifier configured to deliver water vapor or water mist into the periocular air space. In some embodiments, the processor is configured to activate the humidifier when the measured humidity falls below a first specified humidity value. In some embodiments, the headset further includes a dehumidifier configured to remove water vapor from the periocular air space. In some embodiments, the processor is configured to activate the dehumidifier when the measured humidity rises above a second specified humidity value.

In some embodiments, the headset further includes a temperature sensor configured to measure a temperature of the air within the periocular air space. In some embodiments, the processor is configured to read the measured temperature. In some embodiments, the headset further includes a heater configured to heat the air within the periocular air space. In some embodiments, the processor is configured to activate the heater when the measured temperature falls below a first specified temperature value. In some embodiments, the headset further includes a cooling element configured to cool the air within the periocular air space. In some embodiments, the processor is configured to activate the cooling element when the measured temperature rises above a second specified temperature value. In some embodiments, the headset further includes: at least one illuminator capable of illuminating at least one eye of a wearer; and at least one camera configured to capture images of the at least one eye, such that the at least one eye may be scored for severity of dry eye.

In some embodiments, the headset further includes: a humidifier configured to deliver water vapor or water mist into the periocular air space; a dehumidifier configured to remove water vapor from the periocular air space; a heater configured to heat the air within the periocular air space; and a cooling element configured to cool the air within the periocular air space. In some embodiments, the processor is configured to activate at least one of the humidifier, the dehumidifier, the heater, or the cooling element based on the severity of dry eye of the at least one eye. In some embodiments, the headset further includes at least one of: a microfan configured to move air within the periocular air space; a flowrate sensor configured to measure air movement within the periocular air space; a mask to seal the periocular air space against a wearer's face; a temperature sensor configured to measure a temperature of ambient air outside the housing; and a humidity sensor configured to measure a humidity of ambient air outside the housing.

According to another embodiment of the present disclosure, a method for monitoring humidity in a periocular air space of a headset includes: providing a housing configured to define a periocular air space between the housing and at least one eye of a wearer; measuring a physiological parameter of the at least one eye; measuring a humidity of air within the periocular air space; and determining an ophthalmic condition based on the measured humidity and the physiological parameter.

In some embodiments, the method further includes at least one of: activating a humidifier configured to deliver water vapor into the periocular air space when the measured humidity falls below a first specified humidity value; and activating a dehumidifier configured to remove water vapor from the periocular air space when the measured humidity rises above a second specified humidity value. In some embodiments, the method further includes measuring a temperature of the air within the periocular air space. In some embodiments, the method further includes at least one of: activating a heater configured to deliver heat into the periocular air space when the measured temperature falls below a first specified temperature value; or activating a cooling element configured to remove heat from the periocular air space when the measured temperature rises above a second specified temperature value.

In some embodiments, the method further includes at least one of: activating a fan configured to circulate air within the periocular air space when any of a humidifier, a dehumidifier, a heater, or a cooling element are activated; activating the fan configured to circulate air within the periocular air space when a flowrate sensor indicates a flowrate of air within the periocular air space is below a desired flowrate value; providing a mask to seal the periocular air space against a wearer's face; measuring a temperature of ambient air outside the housing; or measuring a humidity of ambient air outside the housing. In some embodiments, the method further includes: illuminating at least one eye of a wearer; capturing images of the at least one eye; and analyzing the images of the at least one eye to score the at least one eye for severity of dry eye. In some embodiments, the method further includes: activating the humidifier, dehumidifier, heater, or cooling element based on the severity of dry eye of the at least one eye.

According to another embodiment of the present disclosure, a system for monitoring humidity in a periocular air space includes: a headset configured to be worn on a face of a wearer, wherein the headset defines a periocular space separate from an ambient air volume; a humidity sensor configured to measure a humidity within the periocular air space; a humidity control element configured to modify the humidity within the periocular space; and a processor configured to: receive the humidity measurement and, in response, to control the humidity control element to modify the humidity within the periocular space; receive a blink rate measurement of the wearer; and determine a dry eye score based on the humidity measurement and the blink rate.

In some embodiments, the humidity control element comprises at least one of: a humidifier configured to deliver water vapor or water mist into the periocular air space, wherein the processor is configured to activate the humidifier when the measured humidity falls below a first specified humidity value; or a dehumidifier configured to remove water vapor from the periocular air space, wherein the processor is configured to activate the dehumidifier when the measured humidity rises above a second specified humidity value. In some embodiments, the system further comprises: a temperature sensor configured to measure a temperature of the periocular air space, and at least one of: a heater configured to deliver heat into the periocular air space, wherein the processor is configured to activate the heater when the measured temperature falls below a first specified temperature value; and a cooling element configured to remove heat from the periocular air space, wherein the processor is configured to activate the cooling element when the measured temperature rises above a second specified humidity value. In some embodiments, the system further includes: an illuminator configured to illuminate at least one eye of a wearer; and a camera configured to capture images of the at least one eye. In some embodiments, the processor is configured to analyze the images of the at least one eye to determine the dry eye score. In some embodiments, the humidifier, dehumidifier, heater, or cooling element are activated based on a severity of dry eye of the at least one eye.

A processor can be configured to perform particular operations or actions by virtue of having software, firmware, hardware, or a combination of them installed on the processor that in operation causes or cause the processor to perform the actions. One or more procedures can be configured to perform particular operations or actions by virtue of including instructions that, when executed by data processing apparatus, cause the apparatus to perform the actions. Other embodiments of this aspect include corresponding processors, apparatus, and instructions recorded on one or more storage devices, each configured to perform the actions of the methods.

The embodiments described herein have particular, but not exclusive, utility for the diagnosis and testing of dry eye and related medical conditions.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the headset periocular temperature and humidity controller, as defined in the claims, is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which:

FIG. 7A is a rear view of a portion of an example headset with an ophthalmic testing unit in accordance with at least one embodiment of the present disclosure.

FIG. 8 is an exemplary pair of pupil camera images from a headset with an ophthalmic testing unit in accordance with at least one embodiment of the present disclosure.

DETAILED DESCRIPTION

Figure 1:
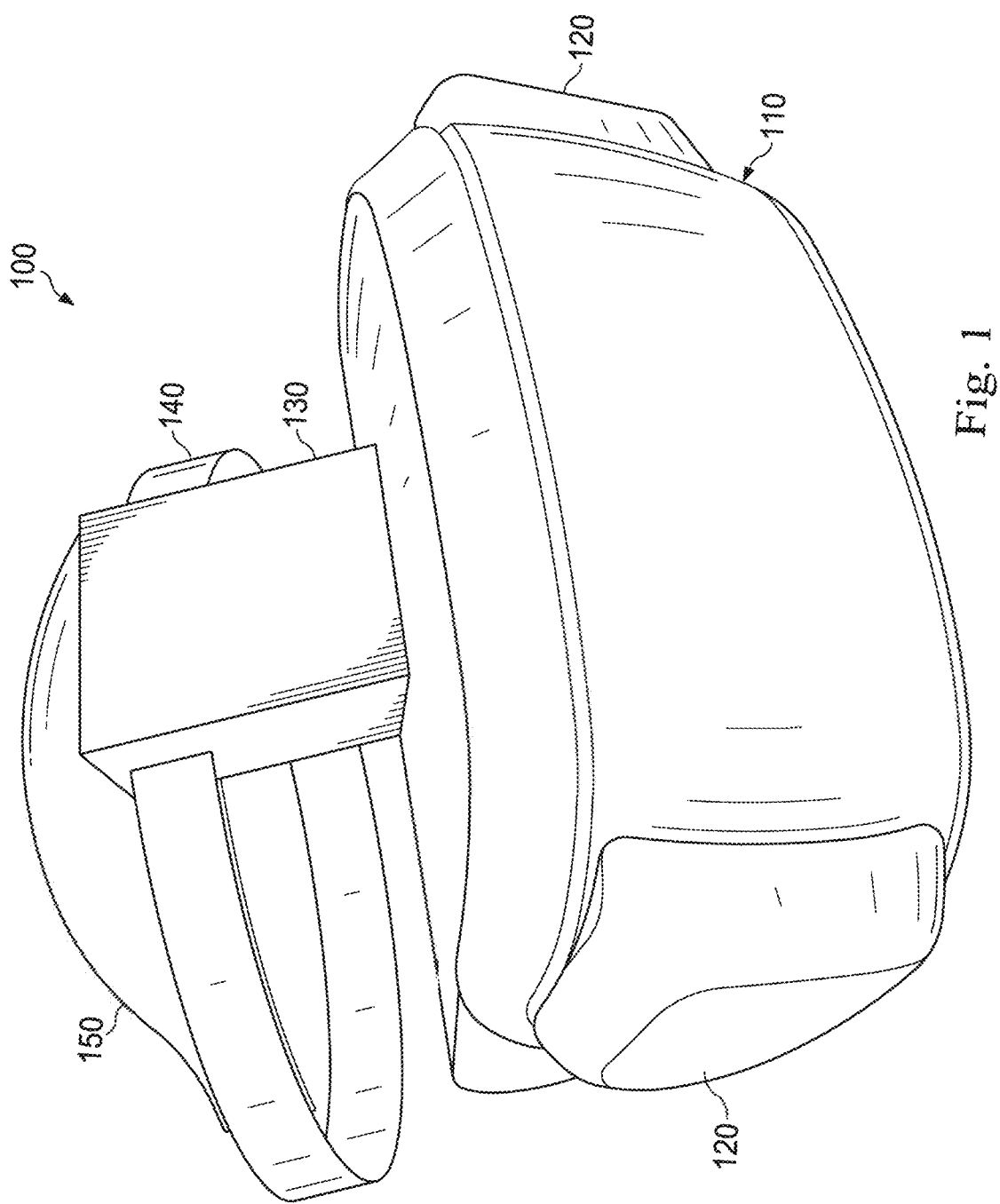
FIG. 1 is a front isometric view of an example headset incorporating a periocular temperature and humidity controller and an ophthalmic testing unit in accordance with at least one embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

In accordance with at least one embodiment of the present disclosure, a headset incorporating a periocular temperature and humidity control unit is provided which is capable of measuring and controlling the temperature and/or humidity of a periocular air space (i.e., a volume of air immediately surrounding the eyes) within a virtual reality (VR), augmented reality (AR), or mixed reality (MR) headset. In some embodiments, the headset further incorporates one or more temperature and/or humidity sensors positioned outside the periocular air space and configured to measure an exterior temperature and/or humidity to be used as a reference point for the internal periocular temperature and/or humidity measurements.

The present disclosure is directed toward measurement and control of humidity and/or temperature of the periocular air space within a headset, for an exemplary purpose of scoring the severity of dry eye under controlled temperature and/or humidity conditions, based on the appearance of specific visual features detected by a camera as described herein.

These descriptions are provided for exemplary purposes only, and should not be considered to limit the scope of the headset periocular temperature and humidity control unit. Certain features may be added, removed, or modified without departing from the spirit of the claimed subject matter.

FIG. 1 is a front isometric view of an example headset 100 incorporating an ophthalmic testing unit and a periocular temperature and humidity control unit in accordance with at least one embodiment of the present disclosure. In the example shown in the figure, the headset 100 includes a display housing 110, two sensor housings 120, a head strap attachment 130, a head strap 140, and a forehead rest 150. In some embodiments, the headset 100 may comprise a virtual reality (VR) headset. In the illustrated embodiment, the sensor housings 120 are coupled to a right and left side of the display housing 110. The sensor housings 120 can be housings for cameras or other optical detection devices, for example. In some embodiments, the sensor housings 120 may include one or more temperature and/or humidity sensors. The sensor housings 120 are in communication with a periocular space within the headset 100 such that one or more sensors (e.g., humidity, temperature sensors) are configured to measure air conditions (e.g., humidity, temperature) of the periocular space within the headset 100. In other embodiments, one or both of the sensor housings 120, or one or more components of the sensor housings 120, may be positioned on the front of the display housing 110, on a top surface of the display housing 110, on a bottom surface of the display housing 110, and/or on the head strap 140. In some embodiments, the headset 100 does not include sensor housings 120 coupled to an exterior of the headset 100. In that regard, electronic components positioned within the sensor housings 120 could be positioned within one or more components of the headset 100, such as the display housing 110, or the head strap 140.

Figure 2:
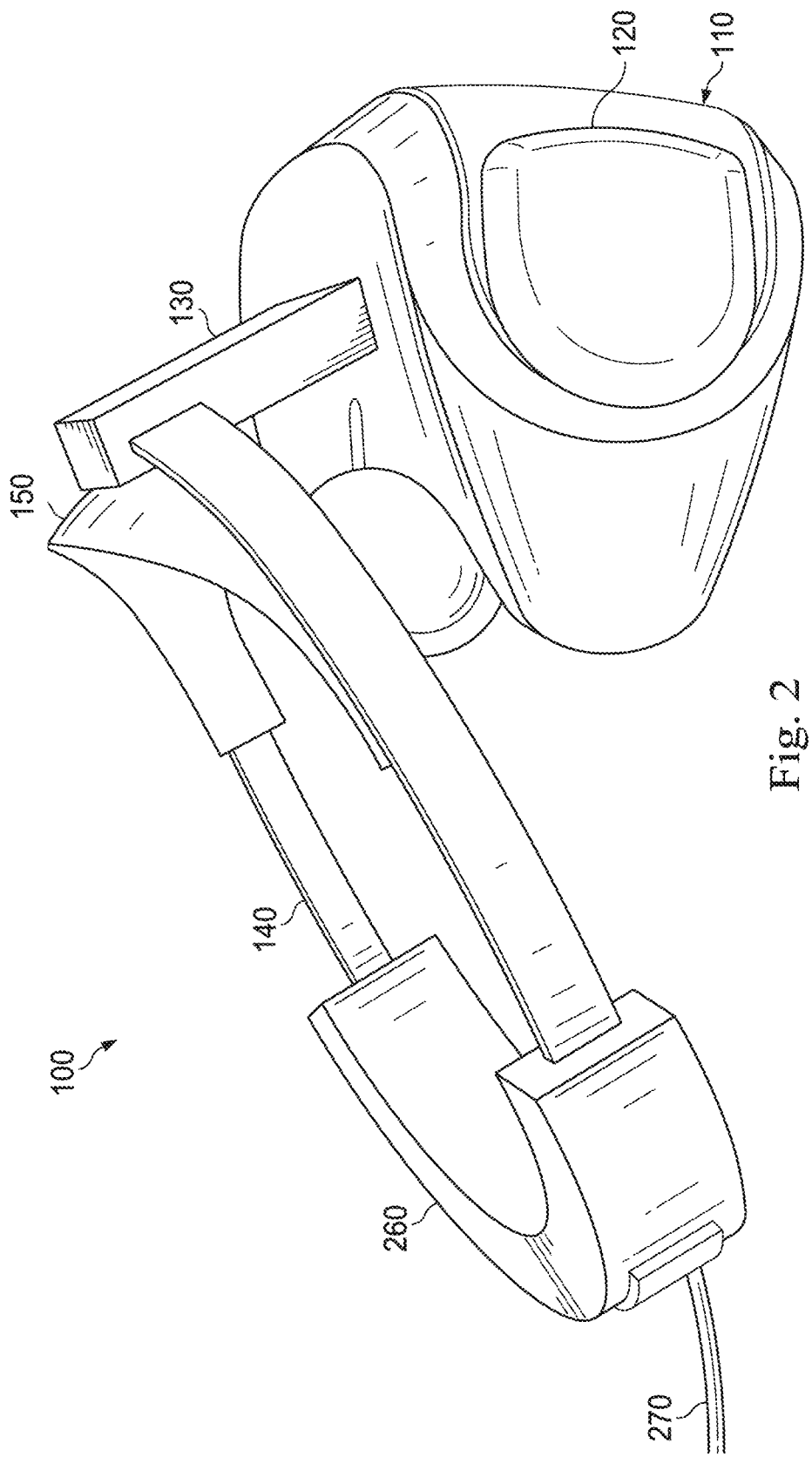
FIG. 2 is a side view of an example headset incorporating a periocular temperature and humidity controller and an ophthalmic testing unit in accordance with at least one embodiment of the present disclosure.

FIG. 2 is a side view of an example headset 100 incorporating an ophthalmic testing unit and a periocular temperature and humidity control unit in accordance with at least one embodiment of the present disclosure. In the example shown, the headset 100 includes a head strap tightener or tension adjuster 260, and a power cord 270. Also visible are the display housing 110, sensor housing 120, head strap attachment 130, head strap 140, and forehead rest 150. It will be understood that, in some embodiments, the headset 100 does not include the power cord 270, but rather includes a battery coupled to the headset 100 and configured to provide electrical power to the components of the headset 100.

Figure 3:
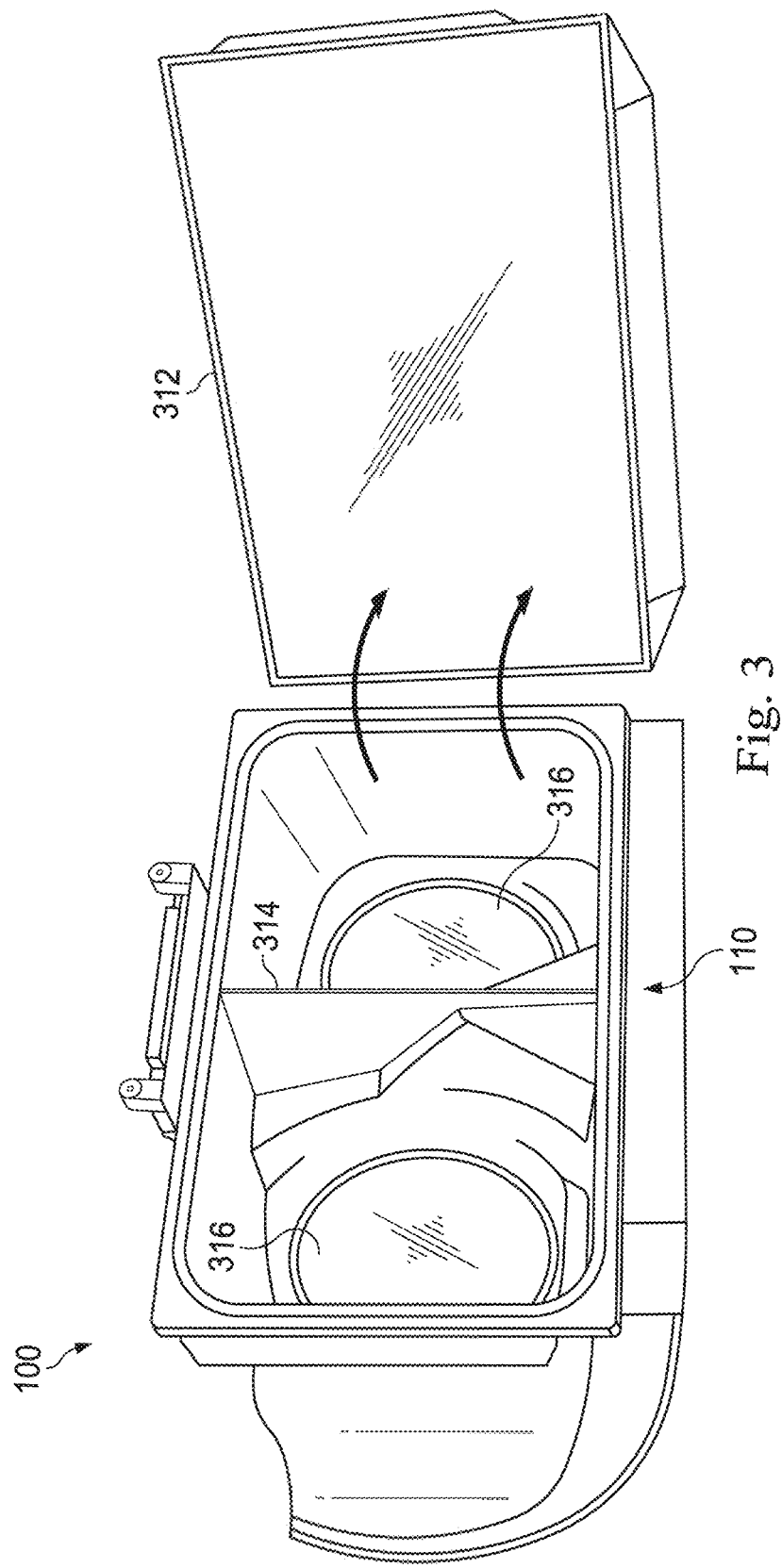
FIG. 3 is an exploded view of a portion of an example headset incorporating an ophthalmic testing unit in accordance with at least one embodiment of the present disclosure.

FIG. 3 is an exploded view of a portion of an example headset 100 with an ophthalmic testing unit in accordance with at least one embodiment of the present disclosure. In particular, FIG. 3 shows an exploded view of a display housing of a headset 100, such as the display housing 110. Shown is a display 312, which attaches to the display housing 110. Also shown is a divider 314 separating the display view between the user's eyes. In an example, the display 312 shows an image through one lens 316, and a slightly different image through the other lens 316, such that the wearer perceives a 3D image. In an example, the headset may also be used to display 2D images, or to display images only to one eye at a time. In other embodiments, the headset 100 does not include the divider 314 and/or the lenses 316.

As explained further below, in some embodiments, the display 312 is configured to display images to the patient or subject while the headset 100 is performing a protocol to test for ophthalmic conditions. In some aspects, the headset 100 can include a periocular temperature and humidity control unit as shown in FIGS. 1 and 2. In some aspects, the display can be used to condition or induce stress in the eye to facilitate testing.

Figure 4:
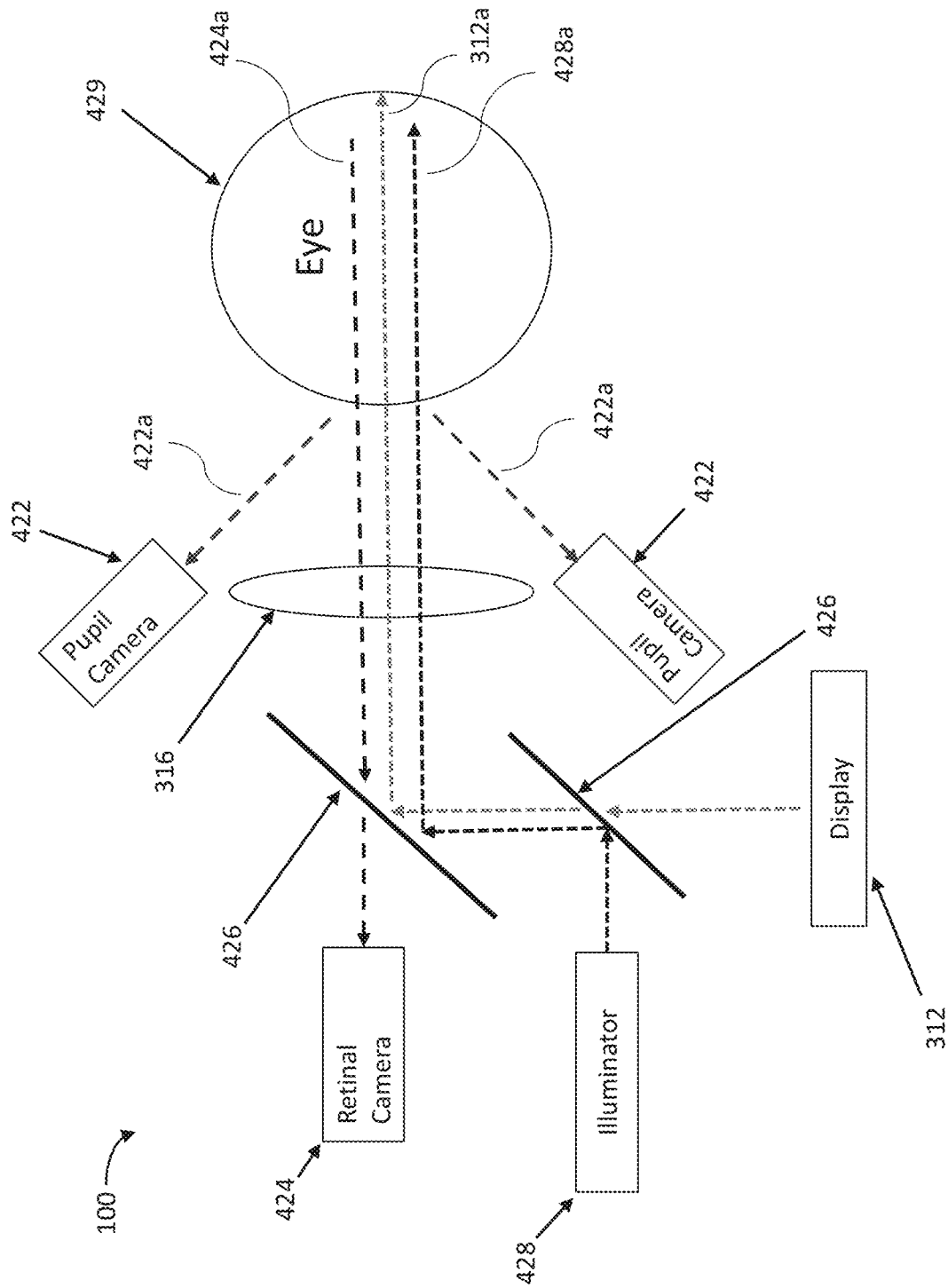
FIG. 4 is a diagrammatic representation of the light paths within an exemplary headset incorporating an ophthalmic testing unit in accordance with at least one embodiment of the present disclosure.

FIG. 4 is a diagrammatic representation of an optical configuration of an ophthalmic testing unit within an exemplary headset 100 for diagnosing and/or grading ophthalmic conditions, in accordance with at least one embodiment of the present disclosure. In that regard, the ophthalmic testing unit shown in FIG. 4 is configured to obtain one or more physiological measurements of an eye, such as blink rate or frequency, blink duration, blink speed or slope, the size/brightness/location of reflections on the surface of the eye, and/or the thickness of the tear film of the eye, including any meniscus and convexivity formed at the edge of the eyelid. The example shown in this figure may include a same or a different configuration than shown in FIG. 3. In the example of FIG. 4, the headset 100 further includes two off-axis pupil detectors 422, a retinal detector 424, two beamsplitters 426, and an illuminator 428. The pupil detectors 422 and/or the retinal detector 424 can include optical detectors, cameras, or any other suitable detector.

In this example, light 312a from the display 312 is not passed directly through the eyepiece lens 316, but instead passes through a first beamsplitter 426 and reflects off of a second beamsplitter 426 before passing through the eyepiece lens 316 and into the eye 429 of the wearer. Light 428a from the illuminator 428 (e.g., infrared light) reflects from a first beamsplitter 426 and a second beamsplitter 426 before passing through the eyepiece lens 316 to the eye 429. The light 428a may be used to illuminate features on or inside the eye 429 that may be imaged or otherwise detected by the pupil detectors 422 or retinal detector 424.

In this example, light 422a reflecting off the surface of the eye 429 passes into the pupil detectors 422 without first passing through any other optical components. However, Light 424a reflecting off the back of the eye passes through the eyepiece lens 316 and a beamsplitter 426 before entering the retinal detector 424.

It should be understood that the pupil detectors 422 may observe other parts of the eye, including but not limited to the eyelids, eyelashes, cornea, intraocular lens, corneal tear film, tear ducts, and Meibomian glands, instead of or in addition to the pupil. It should further be understood that other arrangements of optical components (e.g., illuminators, cameras, beamsplitters, and lenses) may be used to achieve the effects disclosed herein.

Figure 5:
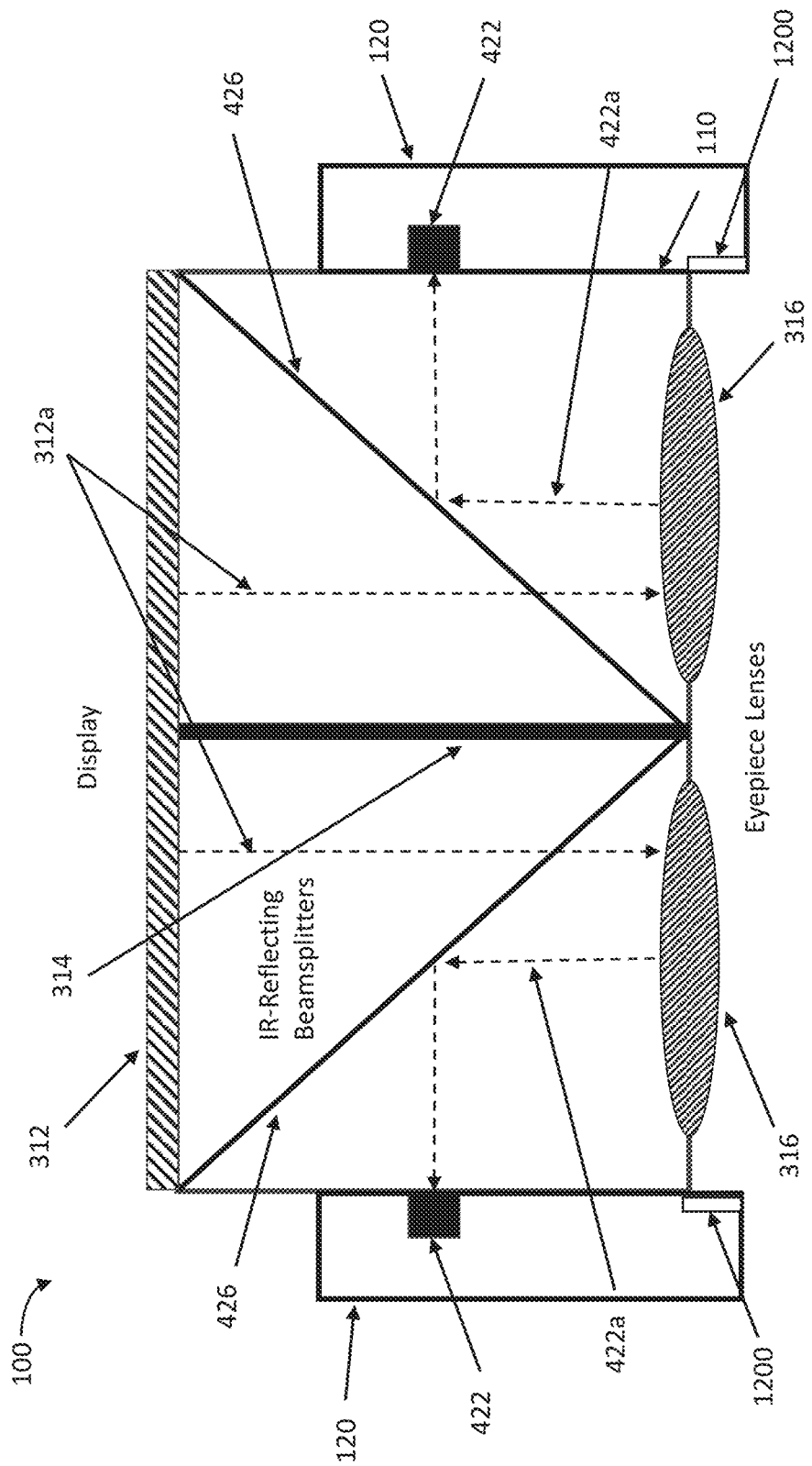
FIG. 5 is a diagrammatic representation of the light paths within an exemplary headset incorporating an ophthalmic testing unit in accordance with at least one embodiment of the present disclosure.

FIG. 5 is a diagrammatic representation of the light paths within an exemplary headset 100 incorporating an ophthalmic testing unit and a periocular temperature and humidity control unit, in accordance with at least one embodiment of the present disclosure. In this example, the display 312, divider 314, two eyepiece lenses 316 and two beamsplitters 426 are situated within the display housing 110. The divider 314 defines two separate regions of the display 312. Each portion of the display emits light 312a (e.g., an image) that passes through a beamsplitter 426 and through an eyepiece lens 316. Light 422a from the illuminator 428 reflecting off the surface of each eye passes through an eyepiece lens 316, reflects off a beamsplitter 426, and into a pupil camera 422, which sits within a sensor housing 120. The source of light 422a which reflects off the surface of the eye may include one or more illuminators, such as IR illuminators 428 (see FIGS. 4, 7A, 7B). In the embodiment shown in FIG. 5, the beamsplitter 426 reflects IR light but does not reflect visible light, such as light provided by the display 312. In other embodiments, such as the embodiment shown in FIG. 4, the beamsplitters 426 reflect IR light and additional light, such as visible light.

Also visible are two periocular temperature and humidity controller circuit boards 1200, located within the sensor housings 120. As described further below, in some embodiments, the temperature and humidity controller circuit boards 1200 may comprise one or more of a humidity sensor configured to measure a humidity within the periocular space of the headset 100, a temperature sensor configured to measure a temperature within the periocular space of the headset 100, a dehumidifier or humidity control element configured to control or adjust the humidity within the periocular space of the headset 100, a heating element, and/or a cooling element. Although more than one temperature and humidity controller circuit boards 1200 are shown in FIG. 5, the headset 100 can include a single temperature and humidity controller circuit board, or multiple temperature and humidity controller circuit boards. Further, in some embodiments, the headset can include one or more temperature and/or humidity sensors in communication with the board 1200 and configured to monitor a temperature and/or a humidity in the external environment around the headset 100.

Figure 6:
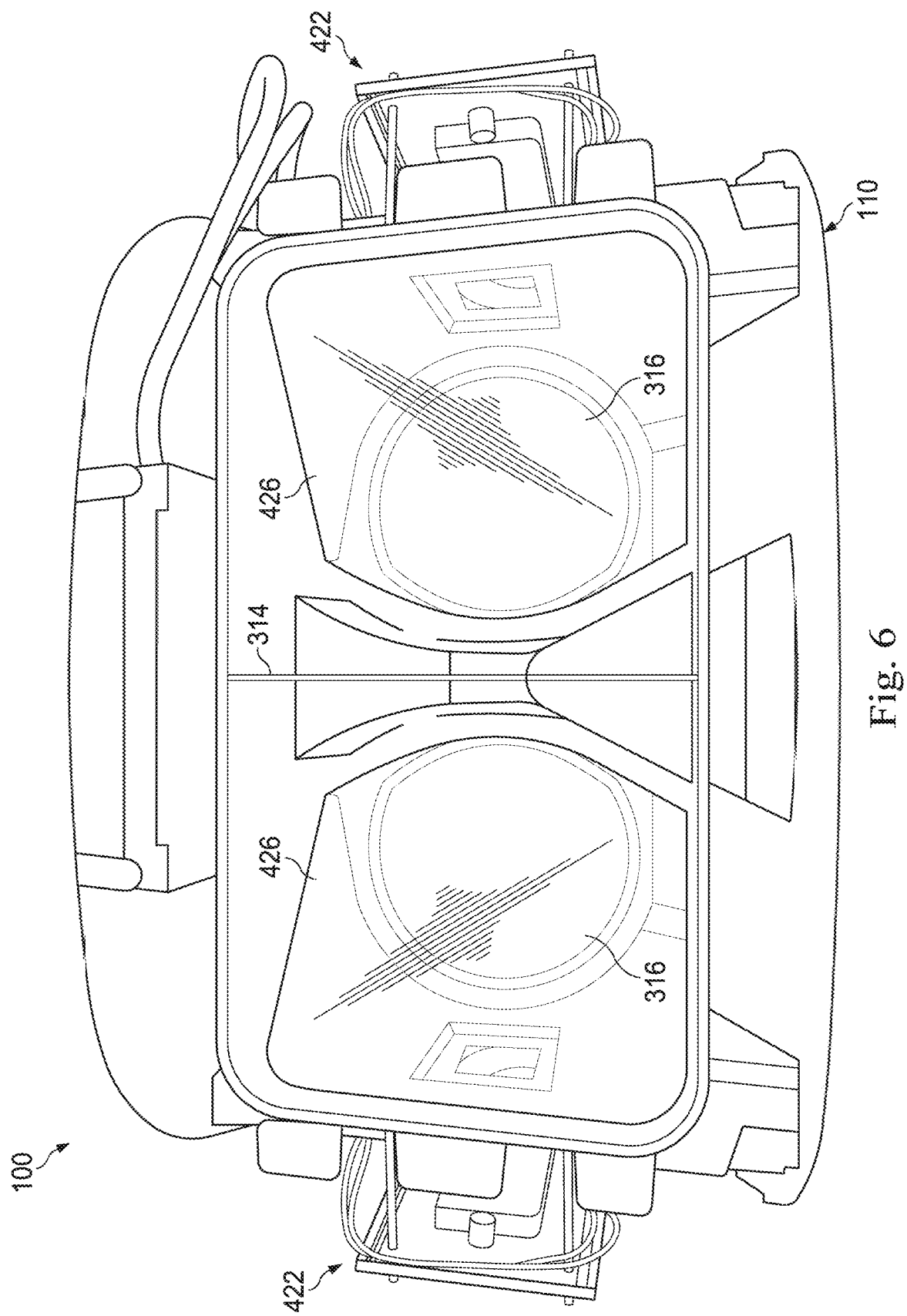
FIG. 6 is a front cutaway view showing optical components in a headset with an ophthalmic testing unit in accordance with at least one embodiment of the present disclosure.

FIG. 6 is a front view of a portion of an example headset 100 with an ophthalmic testing unit in accordance with at least one embodiment of the present disclosure. For clarity, the display 312 has been removed from this view. Visible are the display housing 110, divider 314, two eyepiece lenses 316, two pupil cameras 422, and two beamsplitters 426.

Figure 7B:
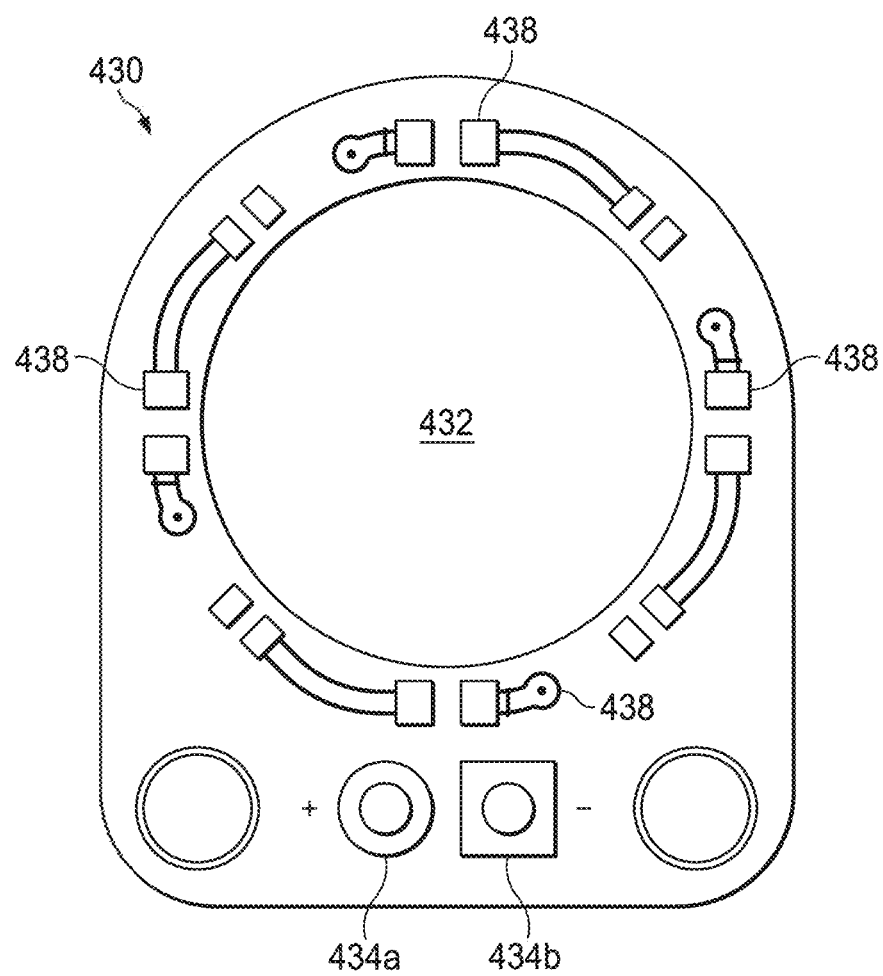
FIG. 7B is a front view of an illuminator assembly for an ophthalmic testing unit in accordance with at least one embodiment of the present disclosure.

FIG. 7A is a rear view of a portion of an example headset 100 with an ophthalmic testing unit in accordance with at least one embodiment of the present disclosure. Visible are the display housing 110, head strap attachment 130, forehead rest 150, and eyepiece lenses 316. Surrounding each eyepiece lens 316 is a plurality of illuminators 428 (e.g., infrared LEDs) that are capable of illuminating the eye for observation by the pupil cameras 422 and/or retinal cameras 424. FIG. 7B shows an illuminator assembly 430, according to an embodiment of the present disclosure. In that regard, the illuminator assembly includes a plurality of illuminators 438 (e.g., infrared LEDs), a positive power connector 434a, a negative power connector 434b, and an aperture or opening 432. In some embodiments, the aperture 432 is positioned around a camera of an ophthalmic testing unit.

FIG. 8 is an exemplary view of a graphical interface for testing or grading ophthalmic conditions. The interface 1000 shows a pair of pupil camera images 1010 from a headset 100 with in accordance with at least one embodiment of the present disclosure. Visible are the corneal tear film 1001, pupil 1002, eyelids 1003, tear ducts 1004, corneas 1006, intraocular lenses 1007, reflections 1008, and computer-generated gaze indicators 1005 at the center of each pupil 1002. In some aspects, the reflections 1008 may represent glints from the illuminators 428. Various features of this image may be used to assess the hydration or dryness of the eyes, including but not limited to blink pattern, blink rate or frequency, blink duration, between-blink interval, blink speed or slope, the size/brightness/location of reflections 1008 on the surface of the eye, and direct observation and measurement (e.g., pixel count and rate of change) of the thickness of the tear film 1001, including any meniscus and convexivity formed at the edge of the eyelid.

Figure 9:
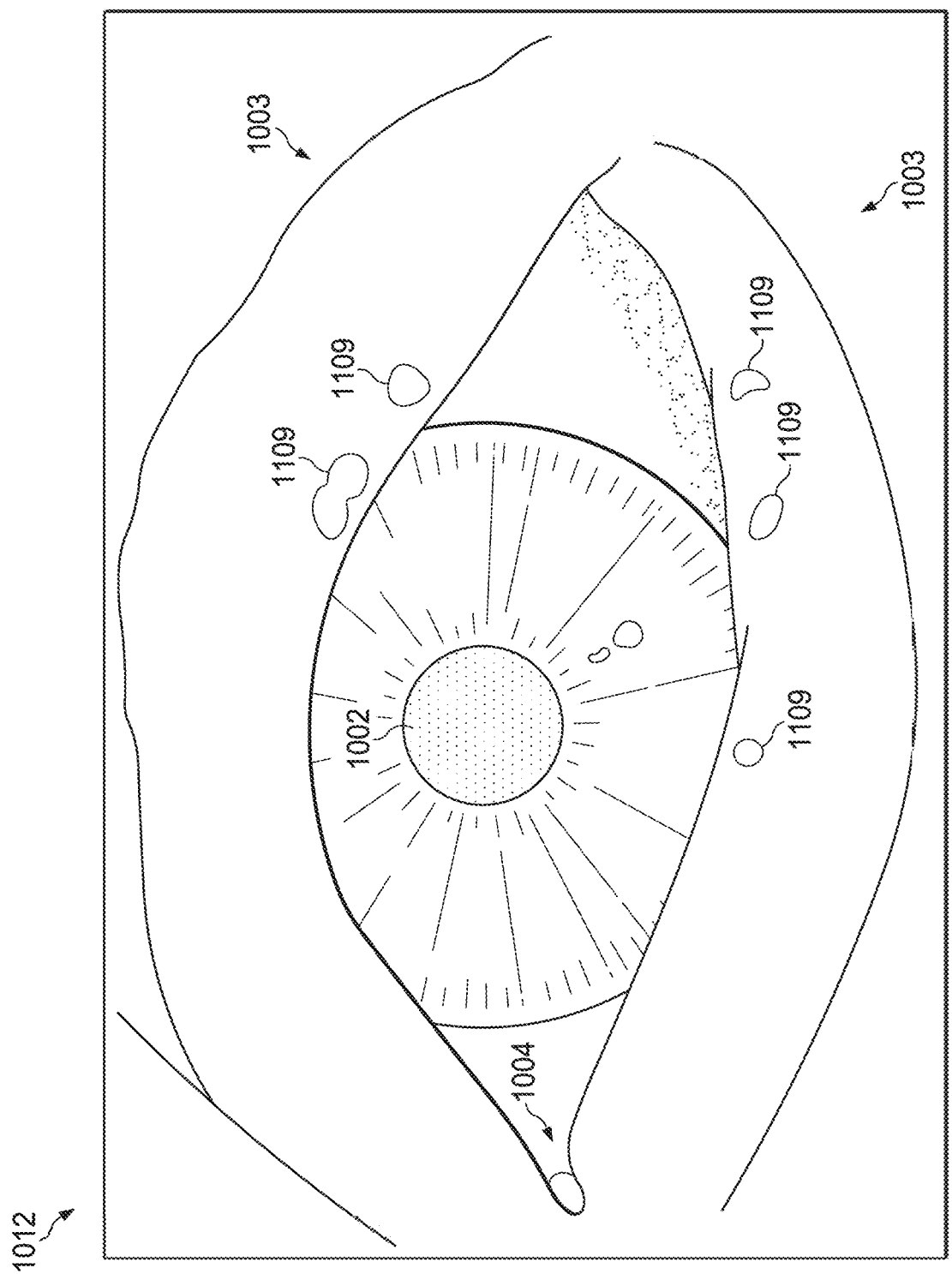
FIG. 9 is an exemplary pupil camera image from a headset incorporating an ophthalmic testing unit in accordance with at least one embodiment of the present disclosure.

FIG. 9 is an exemplary pupil camera image 1012 from a headset 100 with an ophthalmic testing unit in accordance with at least one embodiment of the present disclosure. Visible are the pupil 1002 eyelids 1003, and tear duct 1004. In this example, the wearer has been asked to manually pull open his or her eyelids 1003, revealing Meibomian glands 1009. Irregularities in the Meibomian glands or tear duct may be indicative of both the existence and potential causes of a dry eye problem. Thus, images of the Meibomian glands may be extremely useful in the process of determining a diagnosis and treatment. In addition to automated analysis, such pupil camera images 1000 may be communicated to one or more clinicians, either co-located with the device or in one or more remote locations.

It will be understood that, in some embodiments, circuit boards 1200 for monitoring and/or controlling temperature and/or humidity can be used in conjunction with the ophthalmic testing unit of the headset 100 to improve the accuracy or reliability of measurements obtained by the ophthalmic testing unit. For example, the processor may compensate for temperature and/or humidity in the physiological measurements obtained by the ophthalmic testing unit. For example, the processor may run an algorithm to assess physiological changes, and the algorithm can adjust its output assessing the physiological measurements or changes based on the temperature and/or humidity measured in the periocular space. In that regard, for patients with various dry eye conditions, measurements and grading can be highly dependent on the temperature and humidity of the periocular air space 905. Thus, measuring the temperature and humidity of the periocular air space 905 may permit dry eye readings to be modified or calibrated according to a standardized scale, giving a more accurate understanding of the patient's condition. In some embodiments, a mathematical relationship can be defined and stored in a processor or memory of the headset that uses a physiological measurement and a measured humidity as inputs to determine a corrected or adjusted physiological measurement. In some embodiments, a relationship can be defined in a table whose dimensions include a physiological measurement, a humidity measurement, and/or a temperature measurement. Furthermore, controlling the temperature and humidity of the periocular air space 905 may permit standardized dry eye readings to be taken at a known reference temperature and humidity, allowing for more accurate dry eye readings and scores, and reducing or eliminating the need for calibration of the dry eye readings and scores. For example, a dry eye score may be determined, wherein the dry eye score is an indication of the severity, if any, of dry eye disease.

As an example, a blink rate or pattern may be used for indicating a dry eye or other ophthalmic condition. For example, a blink pattern can be described by a histogram of between-blink intervals over a period of time. Lower mean between-blink intervals may indicate a higher likelihood of a dry eye condition. However, this disclosure recognizes that blink rate varies as a function of environmental conditions, such as temperature and humidity. In some embodiments, a threshold for blink rate may be established, such that a blink rate higher than a threshold indicates that the user or patient has a dry eye or other ophthalmic condition. As recognized in this disclosure, it may be beneficial to calibrate, modify, normalize, or otherwise adjust the blink rate threshold according to the temperature or humidity measured in a periocular air space within a housing of a headset, such as a headset 100 presented herein. As an example, recognizing that blink rate may vary inversely against humidity, a relatively high blink rate may not indicate a dry eye or other ophthalmic condition if the humidity is relatively low. Conversely, a relatively low blink rate may not indicate that a patient does not have dry eye or other ophthalmic condition if the humidity is relatively high. In some embodiments, a processor of the headset can calibrate, modify, normalize, or otherwise adjust a physiological measurement to compensate for variations in humidity and/or temperature. This disclosure recognizes these correlations and presents systems, devices and methods to calibrate measurements to more accurately identify a dry eye condition or other ophthalmic condition. The blink rate is one example of a physiological parameter related to a patient's eye, but the disclosure is not so limited. Generally, a dry eye condition or other ophthalmic condition may be based on any combination of temperature, humidity and physiological measurements.

Figure 10:
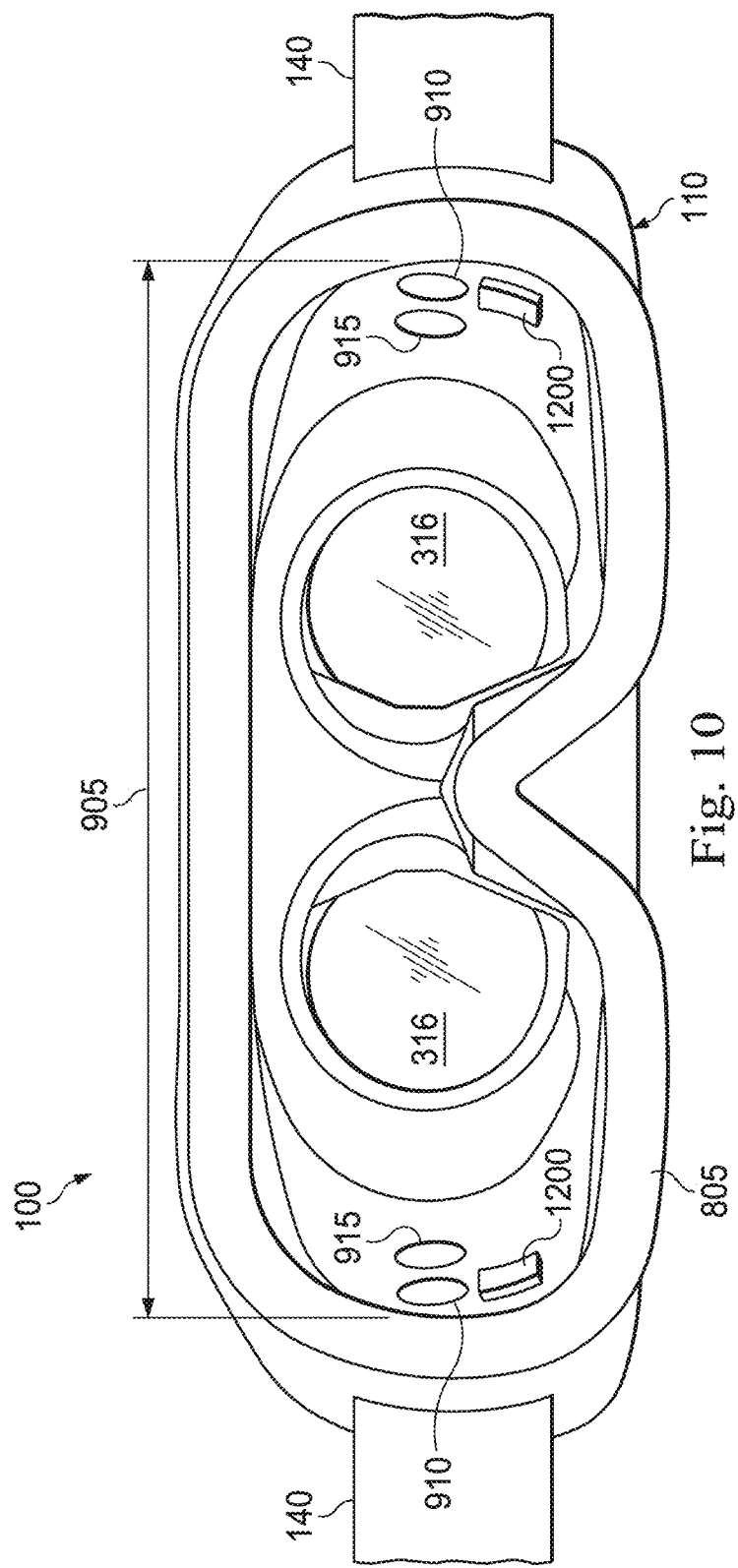
FIG. 10 is a rear view of a portion of an example headset incorporating a periocular temperature and humidity control unit in accordance with at least one embodiment of the present disclosure.

FIG. 10 is a rear view of a portion of an example headset 100 with periocular temperature and humidity controller in accordance with at least one embodiment of the present disclosure. Shown are the display housing 110 with attached face mask 805. Also visible are the head strap 140 and eyepiece lenses 316. Together with the head strap, the face mask 805 forms a periocular air space 905 defined by the wearer's face, the face mask, and the display housing 110, including the eyepiece lenses 316. Also visible are the periocular temperature and humidity control circuit boards 1200, which are capable of measuring and/or altering the temperature and humidity of the air within the periocular air space 905. In some embodiments, the combinations of humidity and/or temperature sensors, dehumidifiers, heating elements, and/or cooling elements allows the humidity and/or temperature to be controlled within the periocular space. In some embodiments, humidity and/or temperature is not controlled by dehumidifiers or heating/cooling elements, but monitored in order to compensate for variations in temperature and humidity due to the external environment, the patient's body heat, and the patient's perspiration. An embodiment of a temperature and humidity control circuit board 1200 is shown and described further below with respect to FIG. 12.

Some embodiments also include one or more microfans 910 to help move or circulate the air in the periocular space, and/or flowrate micromonitors 915 to measure air movement or circulation within the periocular space. In some embodiments, one or more of the circuit boards 1200, the components of the circuit boards, the microfans, the flowrate monitors can be at least partially positioned within one or more housings that are coupled to the display housing 110 and in fluid communication with the periocular space of the headset 100. In some embodiments, one or more of the circuit boards 1200, the flowrate monitors, and/or the microfans can be integrated within the display housing, the head strap, or any other suitable portion of the headset.

Figure 11:
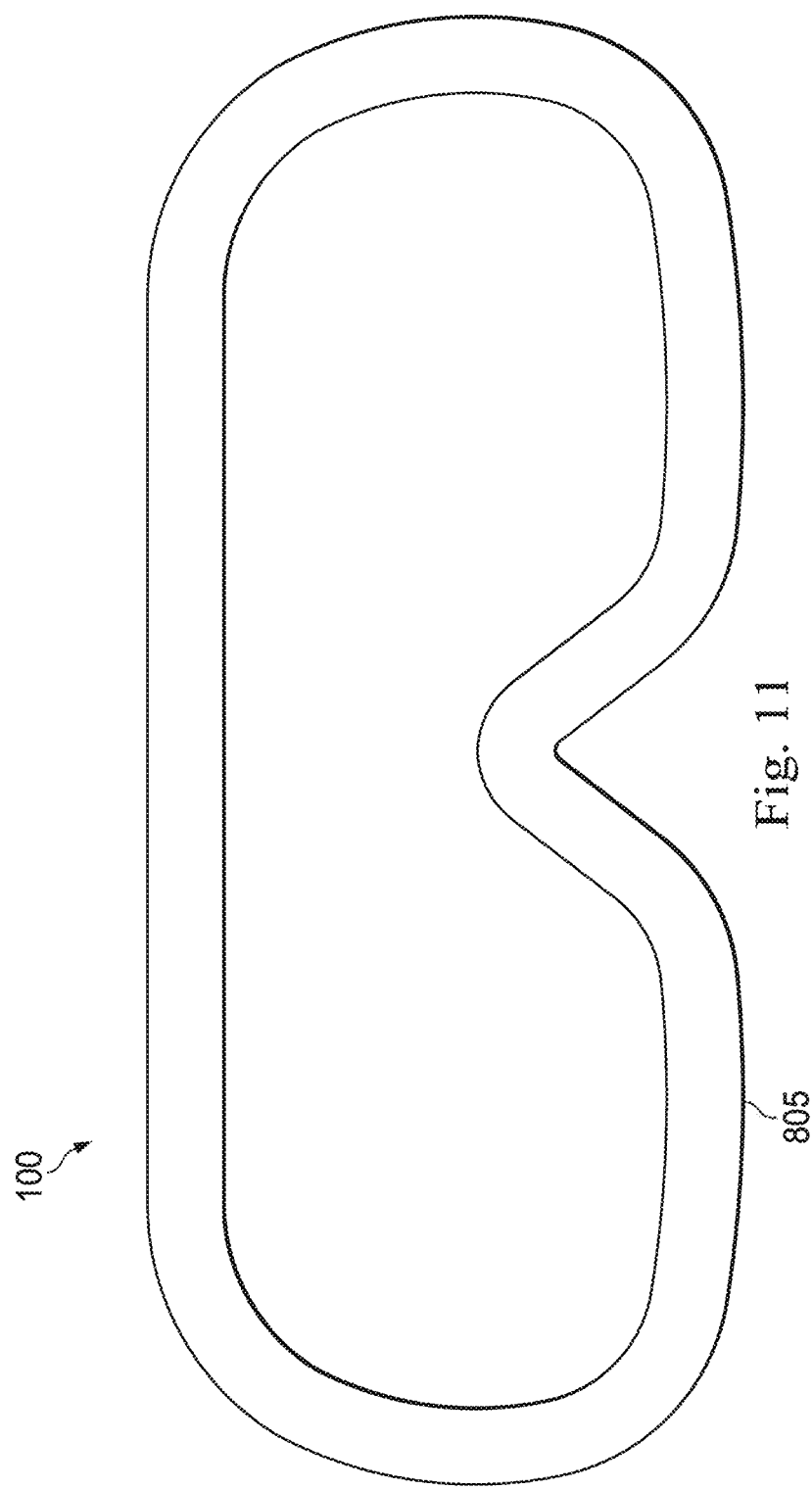
FIG. 11 is an exemplary representation of a face mask for a headset with periocular temperature and humidity control unit in accordance with at least one embodiment of the present disclosure.

FIG. 11 is an exemplary representation of the face mask 805 for the headset 100 shown in FIG. 10. In an example, the face mask helps seal the headset 100 against the wearer's face to prevent the ingress of ambient air into the headset 100 or the egress of periocular air out of the headset 100. In an example, the face mask 805 is made of a soft, compliant, airtight polymer that is easily sterilized, such as silicone or nitrile. In some embodiments, the face mask 805 comprises a foam and/or a rubber material. In some embodiments, the face mask is configured to create an air-tight seal between the periocular space and the external environment. In other embodiments, the face mask creates a barrier but does not create an air-tight seal. In an example, the face mask 805 may be disposable or readily replaceable.

Figure 12:
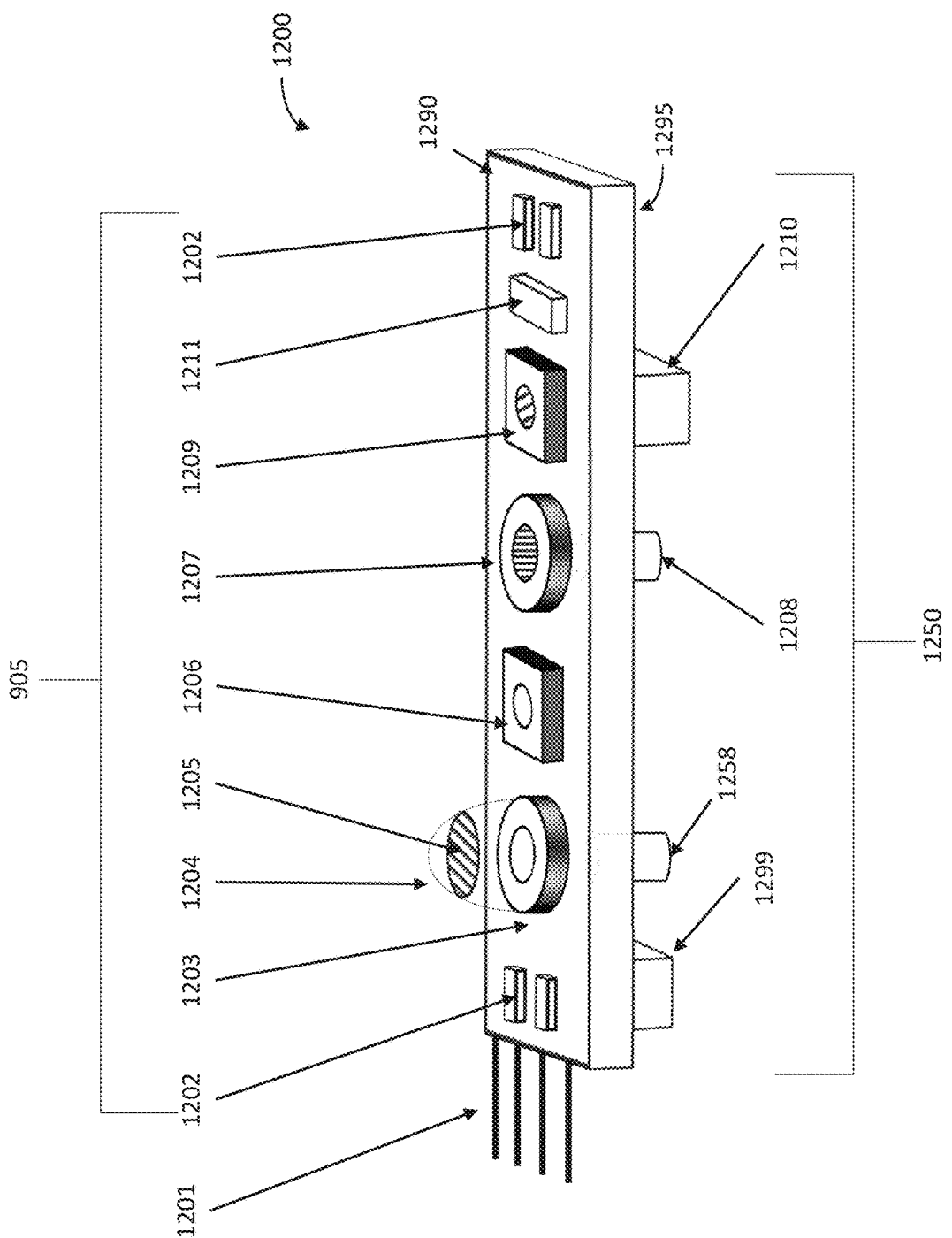
FIG. 12 is an isometric view of an exemplary control circuit board of a headset periocular temperature and humidity control unit in accordance with at least one embodiment of the present disclosure.

FIG. 12 is an isometric view of an exemplary control circuit board 1200 of a headset 100 for monitoring humidity and/or temperature in accordance with at least one embodiment of the present disclosure. In an example, as indicated in FIG. 5 and FIG. 10, the periocular temperature and humidity control circuit board 1200 sits within the sensor housing 120 adjacent to the periocular air space 905. The circuit board 1200 has an inner surface 1290 that faces generally inward toward the periocular air space, and an outer surface 1295 that faces generally outward toward the ambient air 1250 outside the periocular air space 905, and in some cases outside the sensor housing 120. In some embodiments, the sensor housing may include apertures or conduits to connect portions of the control circuit board 1200 directly to either or both of the periocular air space 905 and the ambient air 1250 outside the sensor housing 120, or to connect the periocular air space to the external ambient air (e.g., if ambient air conditions are more favorable than periocular air conditions), with or without fans 910 or flowrate meters 915.

The circuit board 1200 includes wires 1201 which may provide any combination of signals, power, and grounding to the board 1200. The board 1200 also includes electronic components 1202, including but not limited to any combination of electrical traces, signal traces, resistors, diodes, capacitors, inductors, transistors, converters, transceivers, sockets and connectors that may be required to operate the other components of the board 1200.

In the example shown in this figure, the control board 1200 further includes a piezoelectric mister 1203 (e.g., a PZT ultrasonic atomizer film) inside a piezoelectric mister housing 1204 that contains a quantity of water 1205. In an example, the mister housing 1204 includes one or more valves or small apertures that permit mist or water vapor to escape from the mister housing 1204 while causing the water 1205 to be retained within the housing, such that when the piezoelectric mister 1203 is activated, a quantity of water mist or water vapor is expelled at a controlled rate into the periocular air space 905. In some embodiments, the mister housing 1204 also includes a refilling port 1258 accessible on the exterior of the sensor housing 120, through which the water 1205 may be replenished.

In the example shown in the figure, the control board 1200 includes a temperature and humidity sensor 1206, such as an analog temperature and humidity sensor, digital humidity and temperature (DHT) sensor, including a DHT11 and/or DHT22 compliant sensor, that is situated to receive and measure air from inside the periocular air space 905. In some embodiments, the control board 1200 includes a second temperature and humidity sensor 1206 situated to receive and measure ambient air 1250 from outside the headset 100. In some embodiments, the temperature and humidity sensor are packaged as a single component, as shown here. In other embodiments, a temperature sensor and humidity sensor are separate components.

In the example shown in the figure, the controller board 1200 further includes a dehumidifier 1207 (e.g., a Rosahl ionic membrane micro-dehumidifier) that is configured to receive air from within the periocular space 905 and expel moisture into the ambient air 1250 outside the headset 100 through an evaporation port 1208. In this example, the control board 1200 also includes a cooler or cooling element 1209 (e.g., a solid-state thermoelectric cooler) configured to pull heat out of the periocular air space 905 and expel it through a heat sink 1210 situated in the ambient air space 1250 outside the headset 100. The example also includes a heater 1211 (e.g., a solid-state resistive heater) configured to radiate heat into the periocular air space 905. In some embodiments, the thermoelectric cooler 1209 may serve as a heater 1211 simply by reversing the voltage applied across it. In some embodiments, the heat sink is located interior to a sensor housing 120. In other embodiments, the heat sink is located on the exterior of the headset 100 such that it is directly exposed to the ambient environment.

In the example shown in the figure, the control board 1200 includes a processor 1299. The processor may comprise any combination of general-purpose computing devices, reduced instruction set computing (RISC) devices, application-specific integrated circuits (ASICs), or other related logic devices, including mechanical and quantum computers. In some embodiments, the processor comprises a memory in which instructions or information are stored, and the processor operates based on the instructions or information. The memory may be co-located on the same board or chip with processing elements or else located external to a board or chip containing processing elements. The memory may comprise any combination of read-only memory (ROM), programmable read-only memory (PROM), electrically erasable read-only memory (EEPROM), magnetic or electronic random-access memory (RAM), flash memory, disk or tape drive, or other related memory types, The processor 1299 is capable of interpreting sensor readings from the temperature and humidity sensor 1206, and of issuing commands to the piezoelectric mister 1203, dehumidifier 1207, thermoelectric cooler 1209, and heater 1211. Together, the temperature and humidity sensor 1206, humidifier 1203, dehumidifier 1207, and processor 1299 enable closed-loop control over humidity within the periocular air space 905. Together the temperature and humidity sensor 1206, heater 1211, thermoelectric cooler 1209, and processor 1299 enable closed-loop control over the temperature within the periocular air space 905. Closed-loop control over temperature and humidity may enable, for example, dry eye measurements to be taken at a standardized "normal" temperature (e.g., 70° F. or 21° C.) and humidity (e.g., 70% RH), or a standardized "stress test" temperature (e.g., 100 F or 37.7 C) and humidity (e.g., 10% RH), both before and after a particular medication is administered, in order to test the effectiveness of the medication.

In some embodiments, the processor 1299 is also capable of receiving and interpreting pupil camera images 1000 from the pupil cameras 422 in order to measure dry eye variables and eye lubrication of the wearer (see FIG. 10). By incorporating these variables into a control loop, the control board 1200 may exert a degree of direct, closed-loop control over the eye lubrication of the wearer.

In some embodiments, the water reservoir 1205 within the mister housing 1204 is replenished automatically by the dehumidifier 1207, or by an additional dehumidifier 1207 configured to receive ambient air 1250. In some embodiments, the processor is external to the control board 1200, or even to the headset 100. In some embodiments, multiple processors handle different functions of headset with periocular temperature and humidity controller 100. In some embodiments, the functions or components of the headset with periocular temperature and humidity controller 100 are distributed over multiple circuit boards, or are connected separately by wires. In some embodiments, not all of the listed components are included. In some embodiments, additional components are included beyond those listed here. For example, in some embodiments, the control board 1200 is configured to operate one or more microfans 910 or flowrate micromonitors 915 to help circulate heated, cooled, humidified, or dehumidified air within the periocular space 905. In some embodiments, a microfan 910 combined with a desiccant material can serve as, or take the place of, the dehumidifier 1207. In some embodiments, a small, valved tank containing dry air, nitrogen, or other safe dry gases can serve as, or take the place of, the dehumidifier 1207. In some embodiments, the cooler (e.g., a thermoelectric cooler) can induce condensation, reducing the humidity of the periocular air space, and may thus serve as both a cooler and a dehumidifier.

Communication (including but not limited to software updates, firmware updates, or readings from the sensor) to and from the processor 1299 may be accomplished using any suitable wireless or wired communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information, or may display status variables and other information via the display 312.

Communication, if any, within or between components within the headset 100 with periocular temperature and humidity controller may be through numerous methods or protocols. Serial communication protocols may include but are not limited to SPI, I²C, RS-232, RS-485, CAN, Ethernet, ARINC 429, MODBUS, MIL-STD-1553, or any other suitable method or protocol. Parallel protocols may be employed including but not limited to ISA, ATA, SCSI, PCI, IEEE-488, IEEE-1284, and other suitable protocols. Where appropriate, serial and parallel communications may be bridged by a UART, USART, or other appropriate subsystem.

Figure 13:
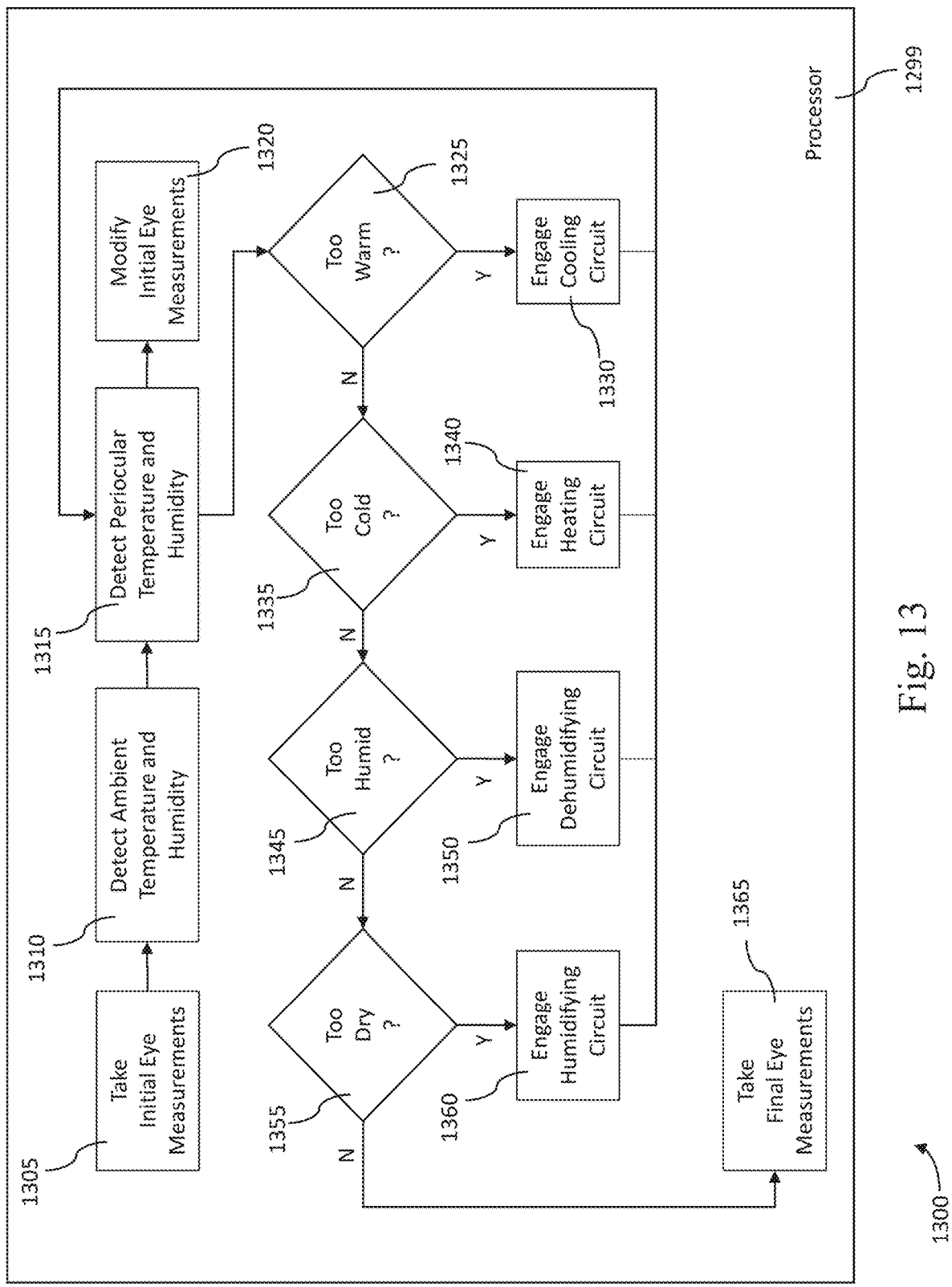
FIG. 13 is a flow diagram showing example process steps taken by a headset periocular temperature and humidity control unit in accordance with at least one embodiment of the present disclosure.

FIG. 13 is flow diagram 1300 showing example process steps 1305-1365 taken by a headset periocular temperature and humidity controller 1200 in accordance with at least one embodiment of the present disclosure. In an example, these steps take place on a processor 1299 that is part of a circuit board 1200 as described above.

In some situations or embodiments, active control of temperature and humidity is not needed or not available, and only steps 1305-1320 are performed. In step 1305, initial measurements of the eye are taken using the pupil camera images 1000 taken by the pupil cameras 422. These measurements may include but are not limited to blink frequency, blink duration, the size/brightness/location of reflections 1008 on the surface of the eye, and direct observation and measurement (e.g., pixel count) of the thickness of the tear film 1001. In step 1310, the temperature and humidity of the ambient air 1250 is detected. Ambient temperature and humidity may drive longer-term changes in eye lubrication by, for example, making it more difficult for the eye to maintain a given lubrication level over the course of a day. In step 1315, the temperature and humidity of the periocular air are measured. Periocular temperature and humidity may drive shorter-term changes in eye lubrication.

For example, when a headset 100 is worn with a sealing face mask 805, the temperature and humidity of the periocular air space 905 may tend to increase over time, such that when a user first puts on the headset 100, eye lubrication is related primarily to the temperature and humidity of the ambient air 1250, whereas over time, eye lubrication may come to be related primarily to the temperature and humidity of the periocular air space 905. In step 1320, the initial eye measurements from step 1305 are calibrated based on the ambient and periocular temperature and humidity, such that a more accurate diagnosis of the patient's condition may be made.

In situations or embodiments where control of the temperature and humidity of the periocular air space 905 is available and desired, steps 1325-1365 may be performed after step 1315. In step 1325, the temperature of the periocular air space is measured against a desired control value or range. If the measured temperature is above the desired or specified value or range, step 1330 is executed, meaning the cooling circuit (e.g., the thermoelectric cooler 1209 from FIG. 12) is activated. At this point, execution returns to step 1315.

If the measured temperature is not above the desired value or range, execution moves to step 1335. In step 335, if a cooling circuit is active, it is deactivated, and the system then determines whether the measured temperature of the periocular air space 905 is below the desired value or range. If yes, execution moves to step 1340, where a heating circuit (e.g., the heater 1211 or polarity-reversed thermoelectric cooler 1209) is activated, and the control loop returns to step 1315. If the measured temperature is not below the desired value or range, execution proceeds to step 1345. In step 1345, if a heating circuit is active, it is deactivated. In this step, the humidity of the periocular air space 905 is checked against a desired value or range. If it is above the desired value or range, step 1350 is executed, wherein a dehumidifying circuit (e.g., the solid-state dehumidifier 1207 from FIG. 12) is activated, and execution returns to step 1315.

If the humidity is not above the specified value or range, step 1355 is executed, where the dehumidifying circuit (if active) is deactivated, and the system determines whether the measured humidity is below the specified value or range. If yes, step 1360 is executed, and a humidifying circuit (e.g., the piezoelectric mister 1203 of FIG. 12) is activated. Execution then returns to step 1315. If the humidity is not below the specified range then the humidifying circuit (if engaged) is deactivated. Both the temperature and humidity are now known to be at desired values or within desired ranges. At this point, step 1365 is executed, wherein a final set of eye measurements are taken under controlled, standardized temperature and humidity conditions that may yield a more predictable and accurate result than measuring under variable ambient conditions.

In this example, in order to save power and limit complexity, only one environmental circuit (cooling, heating, humidifying, or dehumidifying) is activated at a time. In an example, the above control loop executes on a 15-second cycle. However, it should be understood that the control loop may execute at a variety of other speeds, and the controller may be configured to save time by controlling temperature and humidity simultaneously. In an example, to prevent ringing, overshoot, or positive feedback, the controller may be provided with deadbands or hysteresis. In some cases, the controller may hold at the desired temperature and humidity for a period of time (e.g., five minutes) to let the wearer's eyes acclimate before measurements are taken. More complex algorithms may be employed, including object-oriented and real-time algorithms. Some embodiments may be able to select between multiple values or power outputs for the environmental circuits (heating, cooling, humidification, and dehumidification) rather than simply turning them on or off. Some embodiments may account for the interrelationship between temperature and relative humidity, and adjust heating, cooling, humidification, or dehumidification rates accordingly. Some embodiments may control temperature or humidity but not both. Some embodiments may track additional parameters such as the flowrate measured by one or more flowrate micromonitors 915, or may control additional parameters such as the flowrate of one or more microfans 910. In still other embodiments, the control board 1200 may measure or control integrals or derivatives of temperature, humidity, or flowrate.

Accordingly, it can be seen that the headset periocular temperature and humidity controller fills a long-standing need in the art, by permitting precise, closed-loop control over the temperature and humidity of the periocular space within a headset.

A number of variations are possible on the examples and embodiments described above. For example, depending on the implementation, the temperature and humidity controller may incorporate apertures to the ambient air 1250, and may include microfans or flowrate micromonitors to aid in circulation of ambient air into the periocular air space 905.

The technology described herein may be applied to multiple technology areas. In an example, rather than improving ophthalmic measurements of the wearer's eyes, the temperature and humidity control system may be used in virtual reality (VR) games to improve realism by, for example, simulating the feeling of being in a desert, swamp, rainstorm, or dry snowfield. In another example, in various VR, augmented reality (AR), and mixed reality applications (e.g., those used while sitting, standing, walking, or operating a vehicle), the buildup of heat and moisture in the periocular space may become uncomfortable or, alternatively, dry air in the periocular space may contribute to eye fatigue. In these applications, it may be desirable to control the temperature and humidity of the periocular space to ensure maximum user comfort. This may, for example, allow future VR, AR, and MR headsets to fit more snugly against the face (e.g., like ski goggles rather than eyeglasses) to provide better fit and performance without inducing intolerable discomfort.

In some implementations, the water reservoir 1205 may include UV sterilisation diodes or other solid-state radiation generators to limit the growth of bacteria in the water reservoir 1205. It should further be understood that the described technology may be employed in a wide range of ambient temperatures and humidities, such that a single device may yield consistent periocular conditions (and therefore, for example, consistent opththalmic measurements) in different locations around the world.

The language herein should be interpreted as illustrative rather than limiting. Accordingly, the logical elements making up the embodiments of the technology described herein are referred to variously as operations, steps, objects, elements, components, or modules. Furthermore, it should be understood that these may be arranged in any order, unless explicitly claimed otherwise or a specific order is inherently necessitated by the claim language.

All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the headset periocular temperature and humidity controller. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." Unless otherwise noted in the claims, stated values shall be interpreted as illustrative only and shall not be taken to be limiting.

Generally, any creation, storage, processing, and/or exchange of user data associated with the method, apparatus, and/or system disclosed herein is configured to comply with a variety of privacy settings and security protocols and prevailing data regulations, consistent with treating confidentiality and integrity of user data as an important matter. For example, the apparatus and/or the system may include a module that implements information security controls to comply with a number of standards and/or other agreements. In some embodiments, the module receives a privacy setting selection from the user and implements controls to comply with the selected privacy setting. In other embodiments, the module identifies data that is considered sensitive, encrypts data according to any appropriate and well-known method in the art, replaces sensitive data with codes to pseudonymize the data, and otherwise ensures compliance with selected privacy settings and data security requirements and regulations.

The above specification, examples and data provide a complete description of the structure and use of exemplary embodiments of the headset periocular temperature and humidity controller as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter.

Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims.

What is claimed is:

1. A headset for monitoring periocular humidity, comprising:
   a housing configured to be positioned on a user's face, the housing defining a periocular air space;
   a humidity sensor configured to measure a humidity of air within the periocular air space;
   an ophthalmic testing unit configured to measure a physiological parameter of an eye of the user; and
   a processor coupled to the humidity sensor and the ophthalmic testing unit, wherein the processor runs an algorithm to:
   receive the measured humidity and the measured physiological parameter;
   compensate for the humidity of air within the periocular space in the measured physiological parameter, by adjusting the measured physiological parameter based on the measured humidity to produce an adjusted physiological parameter as an output; and
   determine an ophthalmic condition based on the adjusted physiological parameter, wherein the physiological parameter relates to blinking of the eye and the ophthalmic condition corresponds to a dry eye condition.

2. The headset of claim 1, further comprising a humidifier configured to deliver water vapor or water mist into the periocular air space, wherein the processor is configured to activate the humidifier when the measured humidity falls below a first specified humidity value.

3. The headset of claim 1, further comprising a dehumidifier configured to remove water vapor from the periocular air space, wherein the processor is configured to activate the dehumidifier when the measured humidity rises above a second specified humidity value.

4. The headset of claim 1, further comprising a temperature sensor configured to measure a temperature of the air within the periocular air space, wherein the processor is configured to read the measured temperature.

5. The headset of claim 4, further comprising a heater configured to heat the air within the periocular air space, wherein the processor is configured to activate the heater when the measured temperature falls below a first specified temperature value.

6. The headset of claim 4, further comprising a cooling element configured to cool the air within the periocular air space, wherein the processor is configured to activate the cooling element when the measured temperature rises above a second specified temperature value.

7. The headset of claim 1, further comprising:
at least one illuminator configured to illuminate at least one eye of a wearer; and
at least one camera configured to capture images of the at least one eye, such that the at least one eye may be scored for severity of dry eye.

8. The headset of claim 7, further comprising:
a humidifier configured to deliver water vapor or water mist into the periocular air space;
a dehumidifier configured to remove water vapor from the periocular air space;
a heater configured to heat the air within the periocular air space; and
a cooling element configured to cool the air within the periocular air space,
wherein the processor is configured to activate at least one of the humidifier, the dehumidifier, the heater, or the cooling element based on the severity of dry eye of the at least one eye.

9. The headset of claim 1, further comprising at least one of:
a microfan configured to move air within the periocular air space;
a flowrate sensor configured to measure air movement within the periocular air space;
a mask to seal the periocular air space against a wearer's face;
a temperature sensor configured to measure a temperature of ambient air outside the housing; and
a humidity sensor configured to measure a humidity of ambient air outside the housing.

10. A method for monitoring humidity in a periocular air space of a headset, comprising:
providing a housing configured to define a periocular air space between the housing and at least one eye of a wearer;
measuring a physiological parameter of the at least one eye;
measuring a humidity of air within the periocular air space;
accessing memory having stored therein i) a mathematical relationship that uses a physiological measurement and a measured humidity as inputs, to output a corrected or adjusted physiological measurement, or ii) a table that defines a relationship whose dimensions include a physiological measurement and a humidity measurements; and
determining an ophthalmic condition is-based on applying the measured humidity and the physiological parameter to the stored mathematical relationship or the stored table, wherein the physiological parameter relates to blinking of the eye and the ophthalmic condition corresponds to a dry eye condition.

11. The method of claim 10, further comprising providing at least one of:
activating a humidifier configured to deliver water vapor into the periocular air space when the measured humidity falls below a first specified humidity value; and
activating a dehumidifier configured to remove water vapor from the periocular air space when the measured humidity rises above a second specified humidity value.

12. The method of claim 10, further comprising measuring a temperature of the air within the periocular air space.

13. The method of claim 12, further comprising at least one of:
activating a heater configured to deliver heat into the periocular air space when the measured temperature falls below a first specified temperature value; or
activating a cooling element configured to remove heat from the periocular air space when the measured temperature rises above a second specified temperature value.

14. The method of claim 10, further comprising at least one of:
activating a fan configured to circulate air within the periocular air space when any of a humidifier, a dehumidifier, a heater, or a cooling element are activated;
activating the fan configured to circulate air within the periocular air space when a flowrate sensor indicates a flowrate of air within the periocular air space is below a desired flowrate value;
providing a mask to seal the periocular air space against a wearer's face;
measuring a temperature of ambient air outside the housing; or
measuring a humidity of ambient air outside the housing.

15. The method of claim 10, further comprising:
illuminating at least one eye of a wearer;
capturing images of the at least one eye; and
analyzing the images of the at least one eye to score the at least one eye for severity of dry eye.

16. The method of claim 15, further comprising:
activating any of a humidifier, dehumidifier, heater, or cooling element based on the severity of dry eye of the at least one eye.

17. A system for monitoring humidity in a periocular air space, comprising:
a headset configured to be worn on a face of a wearer, wherein the headset defines a periocular space separate from an ambient air volume;
a humidity sensor configured to measure a humidity within the periocular air space;
a humidity control element configured to modify the humidity within the periocular space; and
a processor configured to run an algorithm to:
receive the humidity measurement and, in response, control the humidity control element to modify the humidity within the periocular space into a known reference humidity; and determine a standardized dry eye score while the headset is worn on the face of the wearer and the humidity within the periocular space is at the known reference humidity, wherein determining the standardized dry eye score includes taking a standardized dry eye reading at the known reference humidity, and the standardized dry eye reading relating to blinking of the eye, and the standardized dry eye score indicating a severity of a dry eye condition.

18. The system of claim 17, wherein the humidity control element comprises at least one of:
a humidifier configured to deliver water vapor or water mist into the periocular air space, wherein the processor is configured to activate the humidifier when the measured humidity falls below a first specified humidity value; or
a dehumidifier configured to remove water vapor from the periocular air space, wherein the processor is configured to activate the dehumidifier when the measured humidity rises above a second specified humidity value,
wherein the system further comprises:
a temperature sensor configured to measure a temperature of the periocular air space, and at least one of:
a heater configured to deliver heat into the periocular air space, wherein the processor is configured to activate the heater when the measured temperature falls below a first specified temperature value; and
a cooling element configured to remove heat from the periocular air space, wherein the processor is configured to activate the cooling element when the measured temperature rises above a second specified humidity value.

19. The system of claim 18, further comprising:
an illuminator configured to illuminate at least one eye of a wearer; and
a camera configured to capture images of the at least one eye.

20. The system of claim 19, wherein the processor is configured to analyze the images of the at least one eye to determine the dry eye score; and
wherein the humidifier, dehumidifier, heater, or cooling element are activated based on a severity of dry eye of the at least one eye.

21. The headset of claim 1, wherein the physiological parameter corresponds to at least one of a blink pattern, blink rate or frequency, blink duration, between-blink interval, blink speed, or slope.

22. The headset of claim 1, wherein the processor is further configured to:
assess a physiological change based on the measured physiological parameter.

23. The headset of claim 1, wherein the processor is further configured to:
receive a measured temperature of air within the periocular air space; and
determine the ophthalmic condition by compensating for the temperature in the measured physiological parameter, by adjusting the measured physiological parameter based on a measured temperature.

* * * * *